US012691083B2

(12) United States Patent
Yoon et al.

(10) Patent No.: US 12,691,083 B2
(45) Date of Patent: Jul. 28, 2026

(54) PHARMACEUTICAL COMPOSITION FOR PREVENTING OR TREATING ATTENTION DEFICIT/HYPERACTIVITY DISORDER, CONTAINING KDS2010 AS ACTIVE INGREDIENT

(71) Applicant: DANKOOK UNIVERSITY CHEONAN CAMPUS INDUSTRY ACADEMIC COOPERATION FOUNDATION, Cheonan-si (KR)

(72) Inventors: Bo-Eun Yoon, Yongin-si (KR); Ki Duk Park, Seoul (KR); Jong-Hyun Park, Seoul (KR)

(73) Assignee: DANKOOK UNIVERSITY CHEONAN CAMPUS INDUSTRY ACADEMIC COOPERATION FOUNDATION, Cheonan-si (KR)

( * ) Notice: Subject to any disclaimer, the term of this patent is extended or adjusted under 35 U.S.C. 154(b) by 390 days.

(21) Appl. No.: 18/684,828

(22) PCT Filed: Aug. 19, 2021

(86) PCT No.: PCT/KR2021/011009
§ 371 (c)(1),
(2) Date: Mar. 19, 2024

(87) PCT Pub. No.: WO2023/022256
PCT Pub. Date: Feb. 23, 2023

(65) Prior Publication Data

US 2024/0423932 A1 Dec. 26, 2024

(30) Foreign Application Priority Data

Aug. 19, 2021 (KR) ........................ 10-2021-0109171

(51) Int. Cl.
*A61K 31/165* (2006.01)
*A61P 25/00* (2006.01)

(52) U.S. Cl.
CPC ............ *A61K 31/165* (2013.01); *A61P 25/00* (2018.01)

(58) Field of Classification Search
None
See application file for complete search history.

(56) References Cited

U.S. PATENT DOCUMENTS

2010/0286124 A1 11/2010 Gant et al.
2012/0214742 A1 8/2012 Lee et al.

FOREIGN PATENT DOCUMENTS

KR 10-2005-0085538 A 8/2005
KR 10-2011-0020387 A 3/2011

OTHER PUBLICATIONS

International Search Report of PCT/KR2021/011009 mailed May 16, 2022 from Korean Intellectual Property Office.

Park, Jong-Hyun et al., "Newly developed reversible MAO-B inhibitor circumvents the shortcomings of irreversible inhibitors in Alzheimer's disease", Science Advances, Mar. 20, 2019, vol. 5, article No. eaav03 16, inner pp. 1-12.

Nam, Min-Ho et al., "KDS2010, a newly developed reversible MAO-B inhibitor, as an effective therapeutic candidate for Parkinson's disease", bioRxiv. 2020, inner pp. 1-31 (online publication date: Jul. 7, 2020).

Nam, Min-Ho et al., "Excessive Astrocytic GABA Causes Cortical Hypometabolism and Impedes Functional Recovery after Subcortical Stroke", Cell Reports, Jul. 7, 2020, vol. 32, article No. 107861, inner pp. 1-14.

*Primary Examiner* — Samantha L Shterengarts
(74) *Attorney, Agent, or Firm* — Revolution IP, PLLC

(57) ABSTRACT

The present invention relates to a pharmaceutical composition for preventing or treating attention deficit/hyperactivity disorder (ADHD), containing KDS2010 as an active ingredient, wherein it has been identified, in a Git1 gene-deficient hetero (+/−) mouse, that the amount of GABA is increased in the striatum of the brain, which is in charge of hyperactivity, and thus the mouse can be used as an animal model of ADHD, and it has been identified that inattention and hyperactivity are alleviated upon the administration of KDS2010 to the Git1 gene-deficient hetero (+/−) mouse, and thus KDS2010 is provided as an agent for treating ADHD.

6 Claims, 4 Drawing Sheets

PHARMACEUTICAL COMPOSITION FOR PREVENTING OR TREATING ATTENTION DEFICIT/HYPERACTIVITY DISORDER, CONTAINING KDS2010 AS ACTIVE INGREDIENT

TECHNICAL FIELD

The present disclosure relates to a pharmaceutical composition for preventing or treating attention deficit/hyperactivity disorder (ADHD), including KDS2010 as an active ingredient.

BACKGROUND ART

Attention deficit/hyperactivity disorder (ADHD) is one of the most common mental disorders that first appears in childhood, and it may also occur in adulthood and throughout adulthood. It has been reported that approximately 4.1% of children between the ages of 9 and 17 suffer from ADHD. Infants with ADHD are unable to concentrate on any task and sit quietly, but act impulsively with an inability to complete a task. If left untreated, infants are more likely to be injured, and the disorder has long-term adverse effects on an ability to make friends and a capability in school and/or study of the affected children. Over time, the child with ADHD is more likely to develop depression, poor self-esteem, and other emotional problems.

In most cases, infants and adults with ADHD are treated with psychostimulants such as amphetamines, methylphenidate, and pemoline. Further, antidepressants such as desipramine, which selectively blocks the reuptake of norepinephrine, are also effective in some cases. In addition, new drugs such as atomoxetine that blocks the reuptake of norepinephrine and serotonin may also be effective in treating the disorders. Psychostimulants and monoamine reuptake inhibitors control activity levels and attention, but they are not effective in treating the cognitive deficits associated with or accompanying ADHD.

Causes of ADHD that have been cited include genetic factors, biochemical factors such as lead levels and side reactions to food additives in instant foods, views that there are defects in choosing the right stimuli to the brain, environmental factors such as the relationship between parents and children and the social status of parents, and maternal smoking and alcohol abuse during pregnancy, but the causes are still on the debate. However, neurobiological factors are considered more important than psychosocial factors, and thus research on drug treatment and biological factors for this disease is actively conducted. In particular, it has been suggested that it may be a non-uniform group of diseases caused by abnormalities in the interrelation of various brain regions responsible for higher cognitive functions, rather than abnormalities in the development of a single nervous system due to biological factors. Structural and functional brain imaging studies on children with ADHD up to date have revealed that the pathophysiology of ADHD is generally associated with dysfunction in the fronto-striatal tract, and the drug effect of methylphenidate (MPH) is associated with functional changes in the dopaminergic system in this region. In addition to dopaminergic neurons, symptoms of ADHD are related to the regulation of noradrenaline neurons, which control neural circuits in the frontal lobe. Studies have also reported that ADHD behavior is caused by an imbalance in the regulation of noradrenaline and dopaminergic neurons.

PRIOR ART DOCUMENT

Patent Document

Korean Patent Application Publication No. 10-2005-0085538 (published on Aug. 29, 2005)

DISCLOSURE OF THE INVENTION

Technical Goals

An object of the present disclosure is to provide a pharmaceutical composition for preventing or treating attention deficit/hyperactivity disorder (ADHD), including a component that exhibits an effect of ameliorating hyperactivity.

Technical Solutions

The present disclosure provides a pharmaceutical composition for preventing or treating attention deficit/hyperactivity disorder (ADHD), including KDS2010 or a pharmaceutically acceptable salt thereof as an active ingredient.

In addition, the present disclosure provides a preventive or health functional food composition for attention deficit/hyperactivity disorder (ADHD), including KDS2010 and a foodologically acceptable food supplemental additive.

Advantageous Effects

According to the present disclosure, Git1 gene-deficient hetero (+/−) mice may be used as an animal model for attention deficit/hyperactivity disorder (ADHD) by identifying functional inhibition in the striatum of the brain that controls hyperactivity, and, by identifying that inattention and hyperactivity are ameliorated upon administration of KDS2010 into the Git1 gene-deficient hetero (+/−) mice, KDS2010 may be provided as a therapeutic agent for the attention deficit/hyperactivity disorder (ADHD).

BEST MODE FOR CARRYING OUT THE INVENTION

Figure 1:
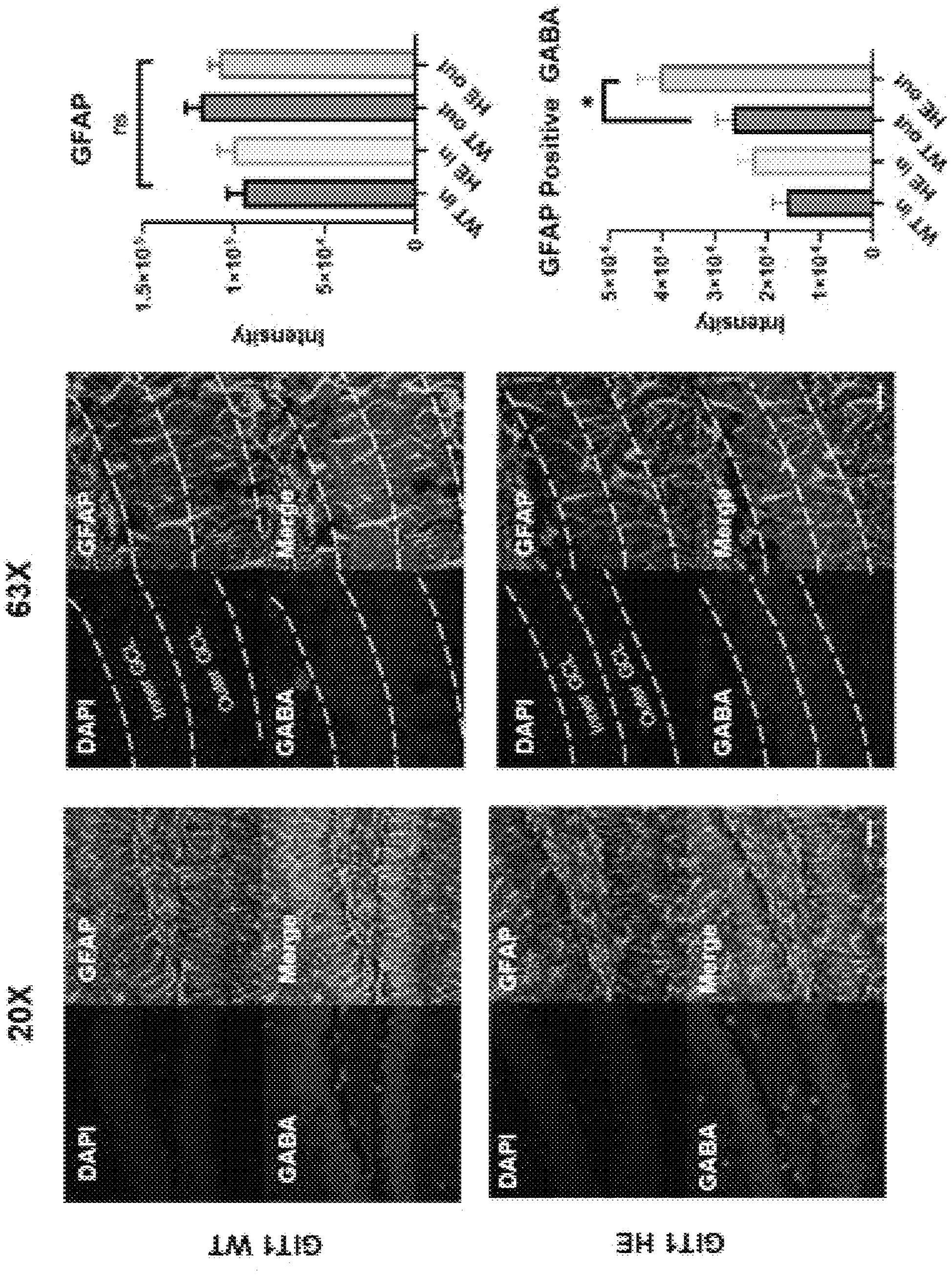
FIG. 1 shows results of evaluating changes in an amount of GABA in an animal model with attention deficit/hyperactivity disorder (ADHD) by fluorescent immunohistochemistry (fIHC).

The terms used herein are selected from general terms that are currently, widely used as much as possible in consideration of functions in the present disclosure, but they may vary depending on the intention or precedent of a person skilled in the art and the emergence of new technology. In addition, in certain cases, there are terms arbitrarily selected by the applicant, in which case their meanings will be described in detail in the corresponding description of the disclosure. Therefore, the terms used herein should be defined based on the meaning of the term and the overall content of the present disclosure, rather than simply the name of the term.

Unless otherwise defined, all terms used herein, including technical or scientific terms, have the same meanings as are generally understood by those skilled in the art to which the present disclosure pertains. Terms such as those defined in commonly used dictionaries should be construed as having meanings consistent with their meanings in the context of the relevant art and should not be construed in an idealistic or excessively formal sense, unless clearly defined in the application.

A numerical range includes values defined in the above range. All maximum numerical limits given throughout the specification include all lower numerical limits, as clearly stated in the lower numerical limits. All minimum numerical limits given throughout the specification include all higher numerical limits, as clearly stated in the higher numerical limits. Any numerical limits given throughout the specification will include all better numerical ranges within a wider numerical range, as the narrower numerical limits are clearly stated.

Hereinafter, the present disclosure will be described in detail.

The present disclosure provides a pharmaceutical composition for preventing or treating attention deficit/hyperactivity disorder (ADHD), including KDS2010 or a pharmaceutically acceptable salt thereof as an active ingredient.

The KDS2010 is a compound represented by the following Chemical Formula 1, specifically (S)-2-(((4'-(trifluoromethyl)-[1,1'-biphenyl]-4-yl)methyl)amino)propenamide.

[Chemical Formula 1]

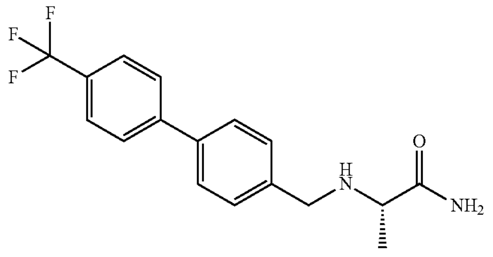

The KDS2010 has an effect of ameliorating concentration deficit and hyperactivity in an animal model with attention deficit/hyperactivity disorder (ADHD).

The pharmaceutically acceptable salts refer to acid additive salts formed by pharmaceutically acceptable free acids, and the pharmaceutically acceptable salts refer to salts commonly used in the pharmaceutical industry, including, for example, inorganic ionic salts made from calcium, potassium, sodium, or magnesium and inorganic acid salts made from hydrochloric acids, nitric acids, phosphoric acids, bromic acids, iodic acids, perchloric acids, or sulfuric acids; organic acid salts made from acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbic acid, carbonic acid, or vanillic acid; sulfonates made from methanesulfonic acid, ethanesulfonic acid, benzenesulfonic acid, p-toluenesulfonic acid, or naphthalenesulfonic acid; amino acid salts made from glycine, arginine, and lysine; or amine salts made of trimethylamine, triethylamine, ammonia, pyridine, or picoline, but the type of salts referred in the present disclosure is not limited by these salts listed.

The pharmaceutical composition of the present disclosure may be prepared in the form of a unit volume by preparation using a pharmaceutically acceptable carrier in accordance with a method that may be easily carried out by those skilled in the art to which the present disclosure pertains, or it may be prepared by introducing in a multi-capacity container.

The pharmaceutically acceptable carriers are those commonly used in preparation, including, but are not limited to, lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present disclosure may additionally include lubricants, humectants, sweeteners, flavoring agents, emulsifiers, suspensions, and preservatives, in addition to the above ingredients.

As used herein, the content of the additives included in the pharmaceutical composition is not particularly limited and may be appropriately adjusted within the content range used in common preparation.

The pharmaceutical composition may be formulated in the form of one or more external agents selected from the group consisting of injectable formulations such as aqueous solutions, suspensions, and emulsions, pills, capsules, granules, tablets, creams, gels, patches, nebulizers, ointments, emplastrums, lotions, liniments, pastas, and cataplasmas.

The pharmaceutical composition of the present disclosure may include additional pharmaceutically acceptable carriers and diluents for formulation. The pharmaceutically acceptable carriers and diluents include, but are not limited to, excipients such as starch, sugars, and mannitol, fillers and extenders such as calcium phosphate, cellulose derivatives such as carboxymethylcellulose and hydroxypropyl cellulose, binders such as gelatin, alginate, and polyvinyl pyrrolidone, lubricants such as talc, calcium stearate, hydrogenated castor oil, and polyethylene glycol, disintegrating agents such as povidone and crospovidone, and surfactants such as polysorbate, cetyl alcohol, and glycerol. The pharmaceutically acceptable carriers and diluents may be biologically and physiologically friendly to a subject. Examples of diluents include, but are not limited to, brine, water-soluble buffers, solvents, and/or dispersion media.

The pharmaceutical composition of the present disclosure may be administered orally or parenterally (e.g., applied intravenously, subcutaneously, intraperitoneally, or topically) depending on the method of purpose. When administered orally, it may be formulated as tablets, troches, lozenges, water-soluble suspensions, oily suspensions, preparation powders, granules, emulsions, hard capsules, soft capsules, syrups, or elixirs. When administered parenterally, it may be formulated as an injection solution, suppositories, powders for respiratory inhalation, aerosols for sprays, ointments, powders for application, oils, and creams.

The dosage of the pharmaceutical composition of the present disclosure may vary depending on the patient's condition and weight, age, sex, health status, dietary constitution specificity, nature of the preparation, severity of disease, administration time of the composition, method of administration, duration or interval of administration, excretion rate, and drug form, and it may be appropriately selected by a person skilled in the art. For example, it may range from about 0.1 to 10,000 mg/kg but is not limited thereby, and administration may be performed once to several times a day.

The pharmaceutical composition may be administered orally or parenterally (e.g., applied intravenously, subcutaneously, intraperitoneally, or topically) depending on the desired method. The pharmaceutically effective amount and effective dose of the pharmaceutical composition of the present disclosure may vary depending on the preparation method of the pharmaceutical composition, the mode of administration, the administration time and/or administration route, and a person skilled in the art may easily determine and prescribe the effective dose for the desired treatment. The administration of the pharmaceutical composition of the present disclosure may be performed once a day or in several divided doses.

In addition, the present disclosure provides a preventive or health functional food composition for attention deficit/hyperactivity disorder (ADHD), including KDS2010 and a foodologically acceptable food supplemental additive.

The present disclosure may be used generally as a commonly used food product.

The food supplemental additives include food additives that are common in the art, e.g., flavoring agents, savoring agents, colorants, fillers, and stabilizers, which are illustrated below.

The food composition of the present disclosure may be used as a health functional food. The term "health functional food" as used herein refers to food manufactured and processed with raw materials or ingredients having useful functionality for the human body in accordance with the Health Functional Food Act, and the term "functionality" as used herein refers to the intake to derive useful effectiveness in health care such as regulation of nutrients or physiological actions for the structure and function of the human body.

The food composition of the present disclosure may include common food additives, and the suitability as the "food additive" is determined by the standards and criteria related to corresponding items according to the general rules and general test methods of Korean Food Additives Codex approved by the Ministry of Food and Drug Safety, unless otherwise stipulated.

The items listed in the "Korean Food Additives Codex" may include, for example, chemically synthesized compounds such as ketones, glycine, potassium citrate, nicotinic acid, and cinnamic acid, natural additives such as persimmon color, licorice extracts, crystallized cellulose, kaoliang color, and guar gum, and mixed preparations such as sodium L-glutamate preparations, noodle-added alkali agents, preservative agents, and tar color agents.

The food composition of the present disclosure may be manufactured and processed in the form of tablets, capsules, powder, granules, liquids, and pills.

For example, hard capsule preparations among health functional foods in the form of capsules may be prepared by mixing and filling the composition according to the present disclosure in conventional hard capsules along with additives such as excipients, and the soft capsule preparations may be manufactured by mixing the composition according to the present disclosure with the additives such as excipients and then filling the same in capsule bases such as gelatin. The soft capsule preparations may include, if necessary, plasticizers such as glycerin or sorbitol, colorants, and preservatives.

The definition of terms for the excipient, binder, disintegrant, lubricant, flavor enhancer, and flavoring agent is described in documents known in the art and includes those having the same or similar functions. The type of food is not particularly limited and includes all health functional foods in the ordinary sense.

The term "prevention" as used herein refers to any action of suppressing or delaying diseases by administering the composition according to the present disclosure. The term "treatment" as used herein refers to any action that improves or favorably changes the symptoms of the disease by administering the composition according to the present disclosure. The term "amelioration" as used herein refers to any action that improves the bad state of the disease by making an individual intake the composition of the present disclosure or administering the same.

Modes for Carrying Out the Invention

Hereinafter, to help understanding of the present disclosure, example embodiments will be described in detail. However, the following example embodiments are merely illustrative of the contents of the present disclosure, and the scope of the present disclosure is not limited to the following example embodiments. The example embodiments of the present disclosure are provided to more completely explain the present disclosure to those of ordinary skill in the art.

Example 1. Preparation of Animal Model with ADHD

Git1 gene-deficient hetero (+/−) mice were prepared as an animal model with attention deficit/hyperactivity disorder (ADHD). Wild-type mice and GIT1 gene-deficient knockout type (KO type) mice were crossed to obtain GIT1 gene-deficient hetero type mice. After making mating cages for among the obtained hetero type mice, genotyping was performed to isolate the hetero type mice.

Example 2. Evaluation on GABA Levels in Animal Model with ADHD

1) Fluorescent Immunohistochemistry (fIHC)

To proceed with fluorescent immunohistochemistry (fIHC), perfusion was performed in mice. Primary perfusion was performed with phosphate-buffered saline (PBS), followed by secondary perfusion by adding 0.05% glutaraldehyde to 4% paraformaldehyde (PFA). Afterwards, the brain was collected from the skull of the mouse, which was then soaked in 4% PFA and stored at 4° C. for half a day (overnight, O/N). The brains of the O/N fixed mice were placed in a 30% sucrose solution and subjected to a drying process for two days. The dried brains were placed in the OCT compound and stored in a mold form at −80° C. After making the mold, the hippocampus was sectioned to a thickness of 30 μm using a cryotome. The sectioned slices were washed with PBS three times for 5 minutes and mixed with triton-X100 and normal goat serum for 1 hour. GFAP and GABA were used as primary antibodies and reacted at 4° C. for half a day (O/N). After the antibody reaction, washing was carried out with PBS three times for 5 minutes, followed by a reaction with fluorescence-conjugated secondary antibodies at room temperature for 2 hours. Washing was performed with PBS three times for 5 minutes, and brain tissues were stained on a slide glass using a DAKO mounting solution.

As shown in FIG. 1, as a result of measuring GABA levels in astrocytes in the Git1 hetero type (+/−) mice, GABA levels were shown to be high in the astrocytes of the outer granule cell layer, where differentiated cells that actually function in the dentate gyrus of the hippocampus are located. The image on the left side in FIG. 1 is a fluorescent image taken by confocal microscopy after fixing sections of brain striatal regions of the Git1 wild type and hetero type mice and then performing fluorescent immunohistochemistry using specific antibodies, wherein DAPI represents the nucleus, GFAP, glial fibrillary acidic protein, represents the astrocytes, and GABA, gamma amino butyric acid, represents the main inhibitory neurotransmitter in the central nervous system. On the right side of FIG. 1 shows a bar graph from the analysis of confocal micrograph images in Image J. The bar graph that analyzed the intensity of GFAP showed no significance, and the intensity of GFAP positive GABA, i.e., GABA in the astrocyte, was shown to significantly increase in the Git1 hetero type. The analysis was performed by dividing into an inner granule cell layer and an outer granule cell layer, and the increase in GABA levels in astrocytes in the outer granule cell layer, which actually functions, suggests that the role of GABA in astrocytes in terms of brain function after development is actually greater.

Example 3. Evaluation on Amelioration in ADHD Upon Administration of KDS2010 in Animal Model with ADHD 1) Passive Avoidance Test The hippocampus, one of the regions that affects ADHD, is responsible for functions related to learning and memory. In order to evaluate the effect of ameliorating ADHD upon administration of KDS2010, KDS2010 was administered to Git1 gene-deficient hetero (+/−) mice, an animal model with ADHD, and a passive avoidance test that enables evaluation on a fear memory learning ability in relation to the function of the dentate gyrus in the hippocampus was conducted. The passive avoidance test was performed using a common passive avoidance test device which was a shuttle box divided into two rooms, one of which was equipped with a bright light bulb to create a bright environment that the laboratory animals dislike, while the other room was designed not to allow light to enter such that the laboratory animals may feel comfortable. After 2 hours of stress application, the passive avoidance response is tested (training test). The floor of a dark room is lined with aluminum rods at regular intervals so as to apply electric shocks to the paws of animals. Laboratory animals tend to enter dark rooms, so if they are placed in a bright room and then enter a dark room, an electric shock (5 V, 0.5 mA, 10 sec) is given to have the animal remember the shock. Immediately thereafter, after 24 hours and after 48 hours, the latency time of entering a dark room without an electric shock is measured up to 90 seconds (retention tests 1, 2, and 3).

The KDS2010 was orally administered at a concentration of 10 mg/kg per day. The amount (mg) of each drug was calculated according to the weight (kg) of each mouse, followed by dissolution in 100 μL of drinking water. Oral administration was performed once a day. The daily amount of water consumed by adult mice older than 7 weeks was administered at a calculated dose of 10 ml/day. The drug was administered 3 days prior to passive avoidance, and the drug administration was continued during the passive avoidance test. KDS2010 is an inhibitor against monoamine oxidase B (MAOB) and may reduce GABA levels that are increased in astrocytes of the hippocampus.

Figure 2:
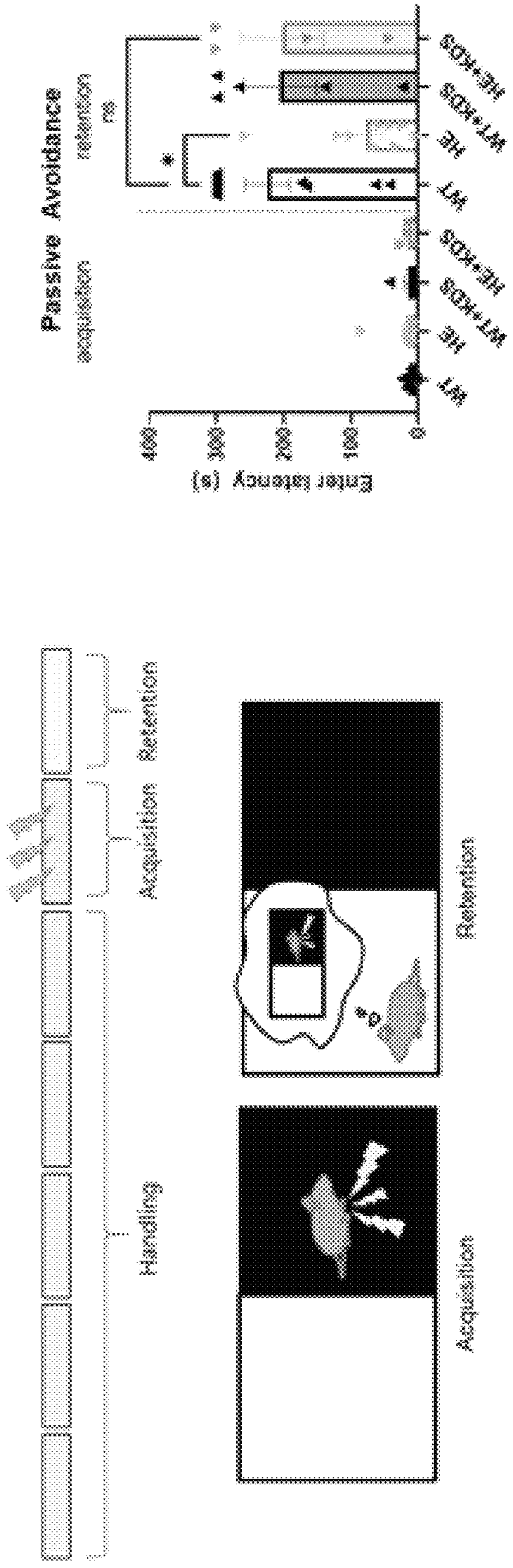
FIG. 2 shows results of evaluating changes in a fear memory learning ability upon administration of KDS2010 in an animal model with attention deficit/hyperactivity disorder (ADHD).
Figure 3:
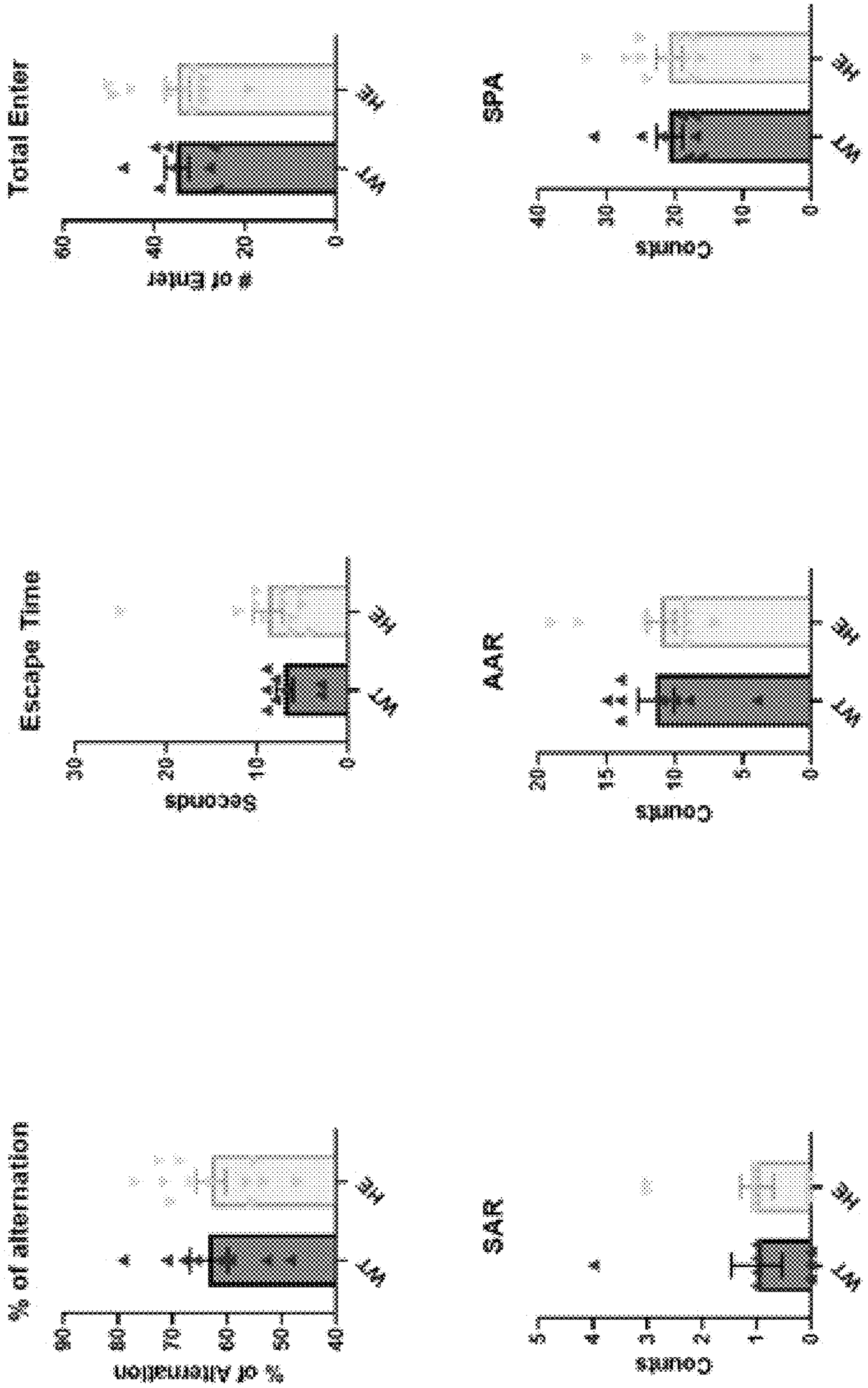
FIG. 3 shows results of evaluating a short-term memory ability of an animal model with attention deficit/hyperactivity disorder (ADHD).

As shown in FIG. 2, the Git1 hetero type (+/−) mice did not remember the electrical stimuli well compared to the wild type (+/+), and the Git1 hetero type (+/−) mice administered with KDS2010 drug showed recovery in the fear memory learning ability, similar to the wild type (+/+) mice. The left side in FIG. 3 shows the experiment schedule and method, and the right side in FIG. 3 shows the average entry time of each group. For acquisition, there was no difference in entry time for each group, but for retention, the time it took for the hetero type to enter the dark room was significantly shorter than that for the Git1 wild type. However, KDS 2010 administration has shown that entry time recovered closer to the wild type.

In other words, the Git1 hetero type mice did not learn fear memory well through electrical stimulation, but it was found that the fear memory learning ability was restored by KDS2010 administration. Learning tests for newly generated fear memories suggest that there was actually a difference shown in the behavior controlled by the dentate gyrus region of the hippocampus in the brain, and the results prove that changes in the amount of tonic GABA may affect the learning ability to induce a recovery effect by KDS2010 when such ability is impaired.

2) Y-Maze Test

A Y-maze test was performed to assess the reliability in memory of the Git1 hetero type (+/−) mice. Prior to the Y-maze test, the mice were handled for 5 days to alleviate stress from experimenters. The Y-maze was installed in a stable place at an appropriate height, and one of the three paths A, B, and C was placed to face the experimenter. After having the mice look at a wall having a short length at a starting point, the time was measured by recording until the mice leave the starting point. Each path that the mice enter was recorded for 5 minutes of the test time. For analysis, the analysis was carried out according to the number of times the mice entered each path and the type of sequence in which the mice entered the path. For example, if the mice enter three different paths in the form of ABC, the mice were considered as having entered spontaneous alteration. If the mice enter a different path once in the form of ABA and then return to the same path, it was considered as an alternate arm return. Finally, if the mice enter the second chosen path in the third time, e.g. in a type of ABB, it was considered as a same-arm return. Those showing the actual short term spatial memory of the mice of each trial were measured by spontaneous alteration (SPA).

After performing Y-maze, the average of the measured values of all the individuals was expressed in the bar graph, and the measured values of each individual were expressed in triangular dots. As shown in FIG. 3, in an experiment conducted in a short term, the Git1 hetero type (+/−) mice showed little difference in all indicators compared to the wild type (+/+) in terms of spatial memory ability. In other words, it proves that the memory of the Git1 hetero type (+/−) mice itself is not bad, and the changes shown in the fear memory learning ability are related to the concentration of mice. It was found that there is a normal function in the short-term spatial memory of the Git1 hetero type. There was no difference between groups in all measured values, including the % of alteration, escape time, number of total enter, number of same arm returns (SAR), number of alternate arm returns (AAR), and number of spontaneous alterations (SPA).

3) Behavioral Evaluation (Open Field Test)

ADHD is diagnosed based on two main tendencies including a hyperactive type and an inattention type, but the two symptoms don't necessarily occur together. From this point of view, hyperactivity-related abilities should not be impaired in the course of treatment for inattention, which has been determined through an open field test that enables measurement of hyperactivity.

An open field test was performed to assess whether there is a behavioral improvement. Handling was performed 5 days before the open field test to minimize the stress that the mice feel from the experimenter. The mice were placed in the center of an open field test cage (30×30×30 cm), and its movement was measured for 10 minutes. The measured videos were analyzed for locomotor activity through ANY-maze.

Figure 4:
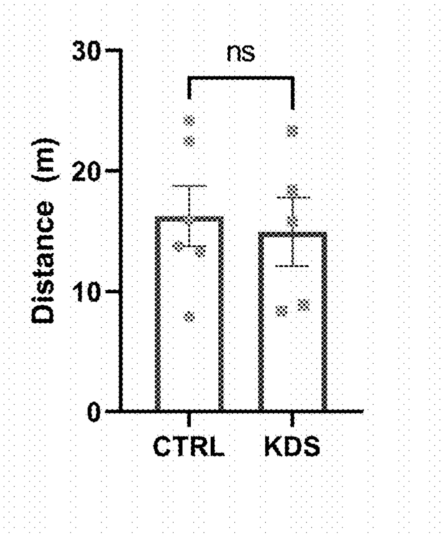
FIG. 4 shows a result of evaluating changes in hyperactivity upon administration of KDS2010 in an animal model with attention deficit/hyperactivity disorder (ADHD).

As shown in FIG. 4, when the Git1 hetero type (+/−) mice were administered with KDS2010 drug, no effect was derived on hyperactivity, although it showed a restorative effect on memory.

4) Self-Grooming

For a self-grooming test, mice were placed in a plastic cylinder with a diameter of 15 cm and a height of 35 cm. In the plastic cylinder, mice were habituated for about 20 minutes, and then self-grooming behavior was recorded for 10 minutes. The duration of the self-grooming behavior was checked through the recorded video, and if there was an interval of 5 seconds, it was measured as different self-grooming. The number of each different self-grooming behavior was expressed as each different self-grooming bout.

Figure 5:
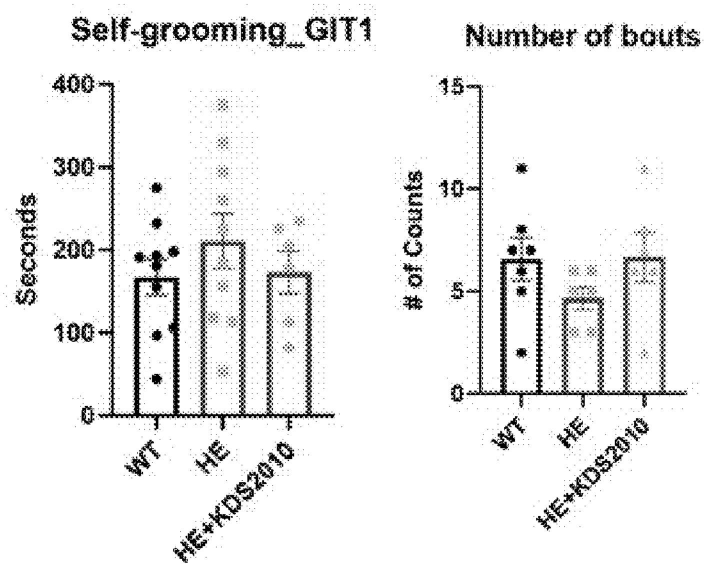
FIG. 5 shows results of evaluating behavioral changes upon administration of KDS2010 in an animal model with attention deficit/hyperactivity disorder (ADHD).

As shown in FIG. 5, the self-grooming duration showed a tendency to increase in the Git1 hetero type (+/−) mice, and when the KDS2010 drug was administered, the self-grooming duration was found to decrease to a value similar to the wild type (+/+) mice.

Having described in detail a specific part of the contents of the present disclosure above, it is clear for those skilled in the art that this specific description is merely a preferred example embodiment, and the scope of the present disclosure is not limited thereby. In other words, the substantial scope of the present disclosure is defined by the appended claims and their equivalents.

The invention claimed is:

1. A method of preventing or treating attention deficit/hyperactivity disorder (ADHD), comprising:

administering a pharmaceutical composition comprising KDS2010 or a pharmaceutically acceptable salt thereof as an active ingredient to a subject.

2. The method of claim 1, wherein the KDS2010 is a compound represented by the following Chemical Formula 1:

[Chemical Formula 1]

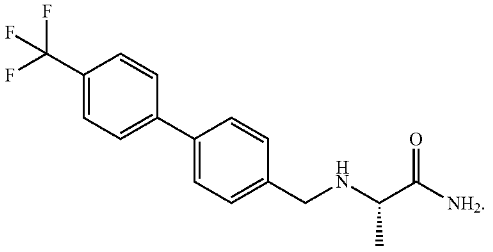

3. The method of claim 1, wherein the KDS2010 ameliorates concentration deficit and hyperactivity.

4. The method of claim 1, wherein the pharmaceutical composition comprises, for formulation, any one or more carriers selected from the group consisting of lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil.

5. A method of preventing or improving attention deficit/hyperactivity disorder (ADHD), comprising:

administering a health functional food composition comprising KDS2010 and a foodologically acceptable food supplemental additive to a subject.

6. The method of claim 5, wherein the KDS2010 is a compound represented by the following Chemical Formula 1:

[Chemical Formula 1]

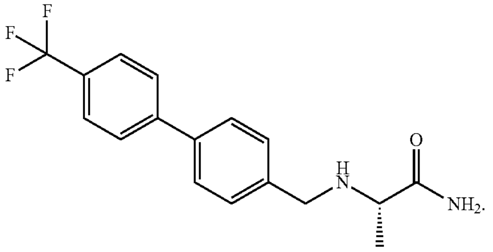

* * * * *